(12) United States Patent
Maki et al.

(10) Patent No.: US 10,166,377 B2
(45) Date of Patent: Jan. 1, 2019

(54) SPINAL TREATMENT METHOD AND SPINAL TREATMENT CATHETER

(71) Applicant: Terumo Kabushiki Kaisha, Tokyo (JP)

(72) Inventors: Toshio Maki, Mishima (JP); Kazuyuki Kurata, Yokohama (JP); Daisuke Nakashima, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/423,865

(22) Filed: Feb. 3, 2017

(65) Prior Publication Data

US 2017/0224969 A1 Aug. 10, 2017

(30) Foreign Application Priority Data

Feb. 8, 2016 (JP) ................................. 2016-022270

(51) Int. Cl.
| | |
|---|---|
| *A61M 29/02* | (2006.01) |
| *A61M 25/09* | (2006.01) |
| *A61M 25/10* | (2013.01) |
| *A61M 25/01* | (2006.01) |
| *A61B 17/34* | (2006.01) |
| *A61B 17/00* | (2006.01) |
| *A61B 17/22* | (2006.01) |
| *A61B 17/32* | (2006.01) |

(52) U.S. Cl.
CPC ............ *A61M 29/02* (2013.01); *A61M 25/09* (2013.01); *A61M 25/10* (2013.01); *A61B 17/3401* (2013.01); *A61B 2017/00261* (2013.01); *A61B 2017/22051* (2013.01); *A61B 2017/320048* (2013.01); *A61M 2025/0183* (2013.01); *A61M 2025/105* (2013.01); *A61M 2025/1079* (2013.01); *A61M 2210/1003* (2013.01)

(58) Field of Classification Search
CPC ............ A61M 29/02; A61M 2025/105; A61M 2025/1079; A61M 2025/0183; A61M 2210/1003
See application file for complete search history.

(56) References Cited

U.S. PATENT DOCUMENTS 4,040,427 A * 8/1977 Winnie .................. A61M 25/02
 604/180
5,509,899 A * 4/1996 Fan .......................... A61L 29/06
 604/103.14
(Continued)

FOREIGN PATENT DOCUMENTS

JP 2002-543870 12/2002
JP 2003/501198 1/2003
(Continued)

*Primary Examiner* — Theodore Stigell
(74) *Attorney, Agent, or Firm* — Jason H. Vick; Sheridan Ross, PC

(57) ABSTRACT

A spinal treatment method and device are provided. The treatment method includes a catheter introduction step of inserting a balloon catheter into a treatment site between nerves extending from a spine, while being bifurcated, and a lesion area that compresses the nerves; and a treatment step of dilating a balloon, on which anti-inflammatory agent is disposed, of the balloon catheter at the treatment site, and applying the anti-inflammatory agent to the treatment site.

20 Claims, 4 Drawing Sheets

(56) References Cited

U.S. PATENT DOCUMENTS

| | | | |
|---|---|---|---|
| 5,788,979 A * | 8/1998 | Alt | A61F 2/062 |
| | | | 424/400 |
| 6,673,362 B2 * | 1/2004 | Calhoun | A61B 17/70 |
| | | | 424/426 |
| 7,718,106 B2 * | 5/2010 | Spencer | A61M 25/0054 |
| | | | 264/261 |
| 8,414,907 B2 * | 4/2013 | Molz | A61L 27/34 |
| | | | 424/423 |
| 2005/0187608 A1 * | 8/2005 | O'Hara | A61L 31/10 |
| | | | 623/1.15 |
| 2015/0088185 A1 * | 3/2015 | Naraghi | A61B 17/0218 |
| | | | 606/192 |

FOREIGN PATENT DOCUMENTS

| | | |
|---|---|---|
| JP | 2009-532078 | 9/2009 |
| WO | WO 00/67650 | 11/2000 |
| WO | WO 00/76409 | 12/2000 |
| WO | WO 2007/106081 * | 9/2007 |

* cited by examiner

SPINAL TREATMENT METHOD AND SPINAL TREATMENT CATHETER

CROSS REFERENCE TO RELATED APPLICATIONS

The present application claims the benefit of priority, under 35 U.S.C. § 119(e), to Japanese Application No. 2016-022270, filed Feb. 8, 2016, entitled "Spine Treatment Methods and Spine Treatment for Catheter," the entire disclosure of which is incorporated herein by reference in its entirety, for all that it teaches and for all purposes.

TECHNICAL FIELD

The present invention relates to a spinal treatment method and a spinal treatment catheter.

BACKGROUND

Currently, not only in Japan, at which super-aged society has arrived, but also in the other countries across the globe that have an aging society, concern for the escalation of medical costs is growing. Examples of the chief complaints of many elderly people include a lumbago and one cause of the lumbago is the spine, so the importance of spinal treatment rises when age progresses.

Various proposals have been conventionally made for spinal treatment. For example, PCT Application Publication No. 2003-501198, which is incorporated herein in its entirety for all that it teaches and for all purposes, discloses removing a bone from an articular process adjacent to a herniated intervertebral disk, and Japanese Patent Application No. JP-A 2002-543870, which is incorporated herein in its entirety for all that it teaches and for all purposes, discloses a filling a fixing substance in a cavity formed by partially scraping an intervertebral disk and a bone adjacent to the disk. Furthermore, Japanese Patent Application No. JP-A 2009-532078, which is incorporated herein in its entirety for all that it teaches and for all purposes, discloses assisting in those manipulations above by the direct visualization of a treatment site.

SUMMARY

Technical Problem

However, through the conventional manipulations as described above, tissues, such as the bone and the intervertebral disk, are removed by resection, scraping, or the like at the treatment site; therefore, these manipulations are highly invasive. Moreover, as a result of the high invasiveness, a recovery period of the treatment site tends to be prolonged, resulting in the escalation of a medical cost.

The embodiments of the present disclosure have been made in the light of these problems and an objective of the embodiments is to provide a spinal treatment method and a spinal treatment catheter capable of ensuring less invasiveness and a low cost.

Solution(s) to the Problems

To achieve the objective(s), a spinal treatment may include: a catheter introduction step of inserting a balloon catheter into a treatment site between nerves extending from a spine (while the nerves are being bifurcated) and a lesion area that compresses the nerves; and a treatment step of dilating a balloon, on which an anti-inflammatory agent is disposed, on the balloon catheter at the treatment site, and applying the anti-inflammatory agent to the treatment site.

To achieve the objective(s), a spinal treatment catheter can include a balloon on which an anti-inflammatory agent is disposed and which can be dilated and deflated, wherein the balloon can be dilated at a treatment site between nerves extending from a spine (while the nerves are being bifurcated) and a lesion area which compresses the nerves.

Advantage(s)

According to the spinal treatment method and the spinal treatment catheter configured as described above, the compression on the nerves is mitigated by the dilation of the balloon and the inflammation of the treatment site is suppressed by the anti-inflammatory agent; therefore, it is unnecessary to perform surgical treatment on the treatment site as in the conventional technique, and thus, the treatment method is less invasive and lower cost than the convention spinal treatment methods.

DETAILED DESCRIPTION

Embodiments of the present disclosure will be described hereinafter with reference to the accompanying drawings. It is to be noted that the scale of the drawings is exaggerated for the convenience of description and differs from an actual scale.

Figure 1:
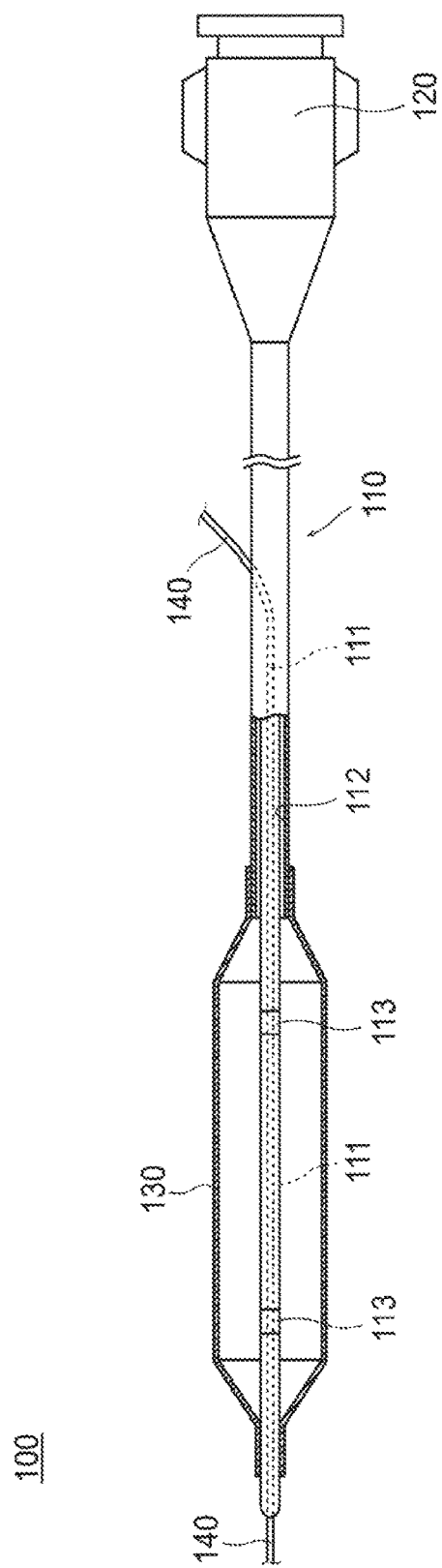
FIG. 1 is a diagram illustrating a schematic configuration of an embodiment of a spinal treatment catheter.

As shown in FIG. 1, a balloon catheter 100 (spinal treatment catheter) can have a main body portion 110, a hub portion 120, and a balloon 130.

The main body portion 110 may have an elongated tubular shape having lumens 111 and 112 formed therein and exhibits flexibility. A guide wire 140 can be inserted into the lumen 111. The lumen 111 is formed on a distal side of the main body portion 110; however, the catheter is not limited to such a rapid-exchange type catheter but may be an over-the-wire type catheter having the lumen 111 formed therein such that the lumen 111 axially penetrates the entire main body portion 110. The lumen 112 extends axially within the main body portion 110 and communicates the hub portion 120 with the balloon 130.

In a distal side portion, where the balloon 130 is provided, of the main body portion 110, markers 113 that exhibit X-ray contrast properties are disposed. A material for forming the markers 113 is not limited to a specific material if the material exhibits X-ray contrast properties, and examples of the material include, but are not limited to: metals (such as platinum, gold, silver, iridium, titanium, and tungsten) and alloys thereof. The markers 113 enable a position of the balloon 130 in the body to be located using X-ray imagery.

The hub portion 120 is provided on a proximal end of the main body portion 110 and is connectable to a pressure application instrument, for example, an indeflator. The hub portion 120 communicates with the lumen 112.

The balloon 130 is provided on an outer periphery of the distal side of the main body portion 110 and can be dilated and deflated. A working fluid such as a physiological salt solution is pressurized and supplied through the lumen 112 to the balloon 130 from the pressure application instrument that is connected to the hub portion 120, thereby dilating the balloon 130. Furthermore, a negative pressure is applied by the pressure application instrument to discharge the working fluid through the lumen 112, thereby deflating the balloon 130.

The balloon 130 is inserted into the spine and come in contact with a bone or the like, so that a material for forming the balloon 130 is preferably not only flexible but also difficult to burst. Examples of the material for forming the balloon 130 include, although not being limited thereto, vinyl chloride, polyurethane, polyurethane elastomer, styrene-ethylene-butylene-styrene copolymer (SEBS), styrene-ethylene-propylene-styrene copolymer (SEPS), ethylene-vinyl acetate copolymer (EVA), and polyamide resin and polyamide elastomer such as nylon, polyester resin and polyester elastomer such as polyethylene terephthalate (PET), olefin-based resin such as polyethylene, rubber, silicone elastomer, fluorocarbon rubber, and fluorocarbon resin.

An anti-inflammatory agent can be coated onto an outer peripheral surface of the balloon 130. The anti-inflammatory agent is, for example, salazosulfapyridine; however, the anti-inflammatory agent is not limited thereto and other medicines, such as dexamethasone or prednisolone, may be used.

The anti-inflammatory agent may be coated, together with another substance(s), for example, phosphatide, to the surface of the balloon 130 in the form of laminae, for example. Note that the phosphatide is at least one type selected from a group comprising, for example, phosphatidylcholine, phosphatidylglycerol, phosphatidic acid, phosphatidyl ethanolamine, phosphatidyl serine, phosphatidyl inositol, phosphatidyl inositol polyphosphoric acid, sphingomyelin, cardiolipin, partially hydrogenated additives thereof, and fully hydrogenated additives thereof. The phosphatide helps the anti-inflammatory agent efficiently move into the cells.

A spinal treatment method will next be described.

Figure 2:
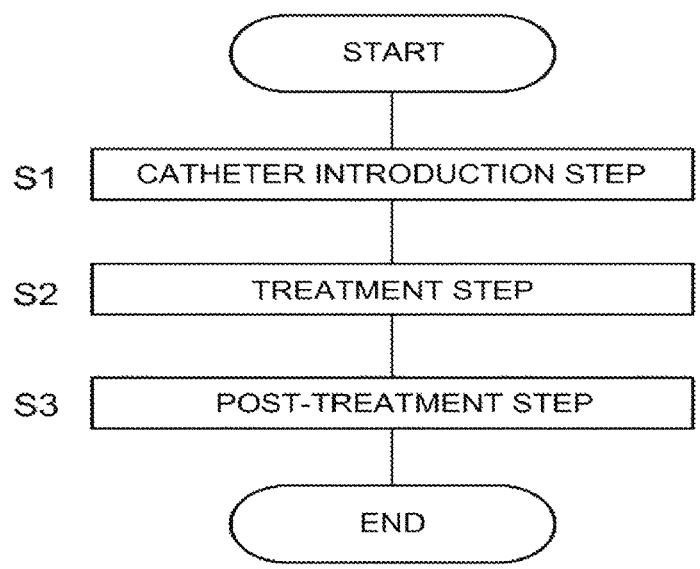
FIG. 2 is a flowchart of an embodiment of a spinal treatment method.

As shown in FIG. 2, the spinal treatment method can include a catheter introduction step S1, a treatment step S2, and a post-treatment step S3, which may implemented for the treatment of a hernia of an intervertebral disk.

Figure 3:
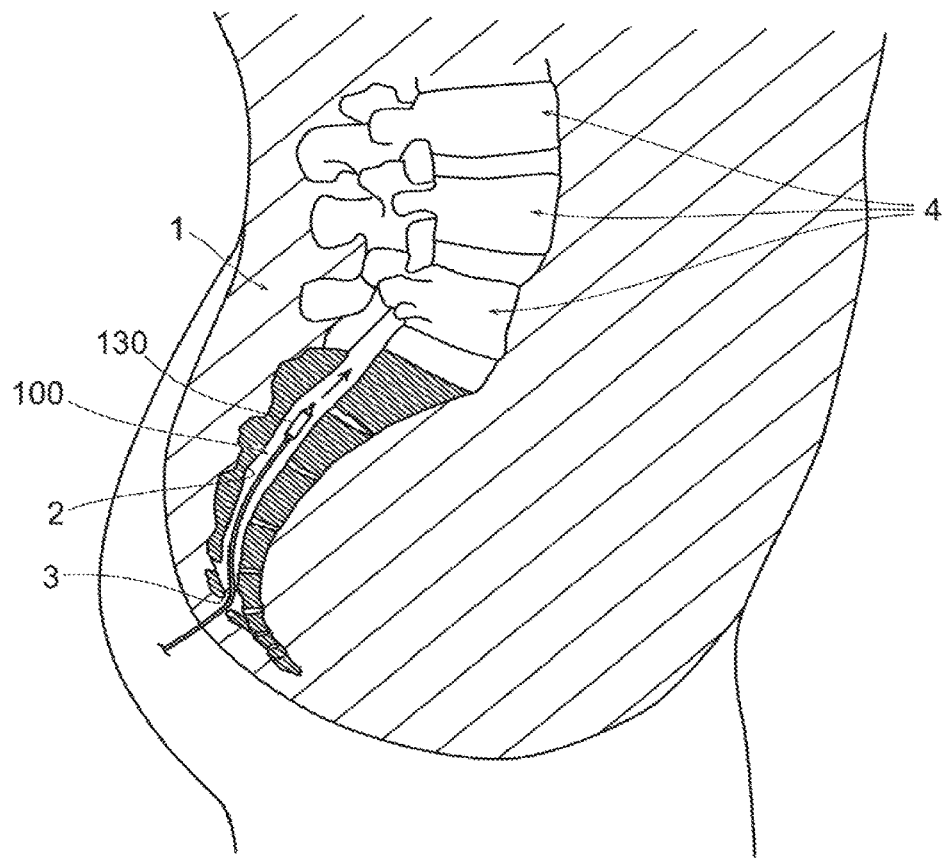
FIG. 3 is a view illustrating the insertion of the spinal treatment catheter into the sacrum.

As shown in FIG. 3, in the catheter introduction step S1, an operator can introduce the balloon catheter 100 into a target treatment site through a spine 1.

Specifically, the operator introduces the balloon catheter 100 through a sacral canal 2. For example, the operator punctures, with a puncture instrument (not shown) having a lumen formed therein, toward a sacral hiatus 3 to communicate (open) the sacral canal 2 with the outside of the body, and introduces the balloon catheter 100 into the sacral canal 2 through this puncture instrument.

A poriform wound formed by such a puncture instrument is small and it is unnecessary to make a large incision in the body to introduce the balloon catheter 100 into the body; therefore, it is possible to keep lessen the invasiveness of the procedure for a patient.

The operator moves the balloon catheter 100 from the sacral canal 2 to lumbar vertebrae 4 to move the balloon catheter 100 forward to the target treatment site. Although not shown, the operator has moved the guide wire 140 to the target treatment site prior to the balloon catheter 100, and moves the balloon catheter 100 forward along the guide wire 140.

The balloon catheter 100 is introduced into the body in a state where the balloon 130 has been deflated. An outer diameter of the balloon 130 in the deflated state is equal to or smaller than gaps of the sacral hiatus 3 and the sacral canal 2, so that the balloon 130 in the deflated state can be inserted thereinto. The outer diameter of the balloon 130 in the deflated state is, for example, 0.5 to 3 mm.

Figure 4:
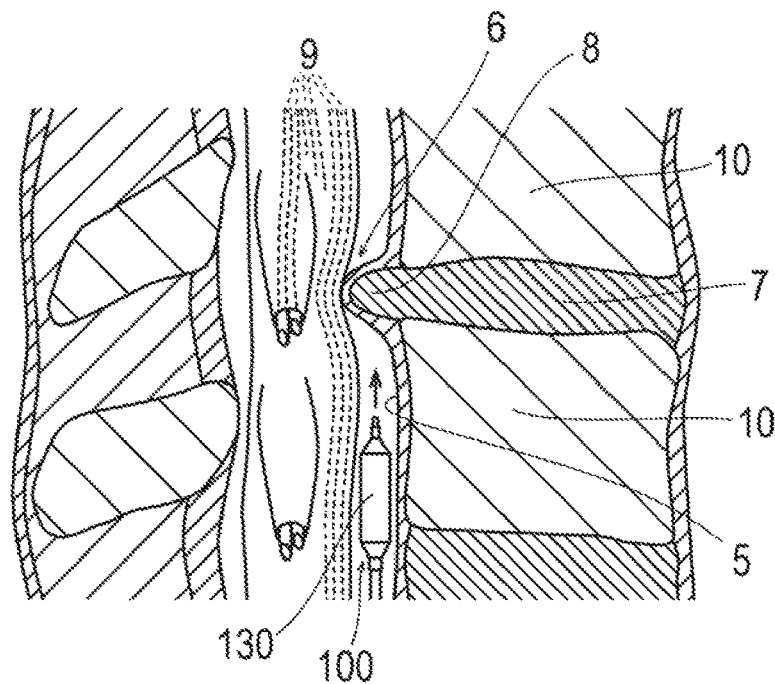
FIG. 4 is a view illustrating the movement of the spinal treatment catheter to a treatment site.

As shown in FIG. 4, the balloon catheter 100 moves from the sacrum side and arrives at a target treatment site 6 by way of an epidural space 5. The balloon 130 in the deflated state can be inserted into the epidural space 5.

At the treatment site 6, a lesion area 8 formed after the intervertebral disk 7 is herniated compresses the cauda equina 9 (nerves extending from the spine while being bifurcated). The lesion area 8 protrudes from between vertebral bodies 10 that form a part of the spine 1 and compress the cauda equina 9.

Figure 5:
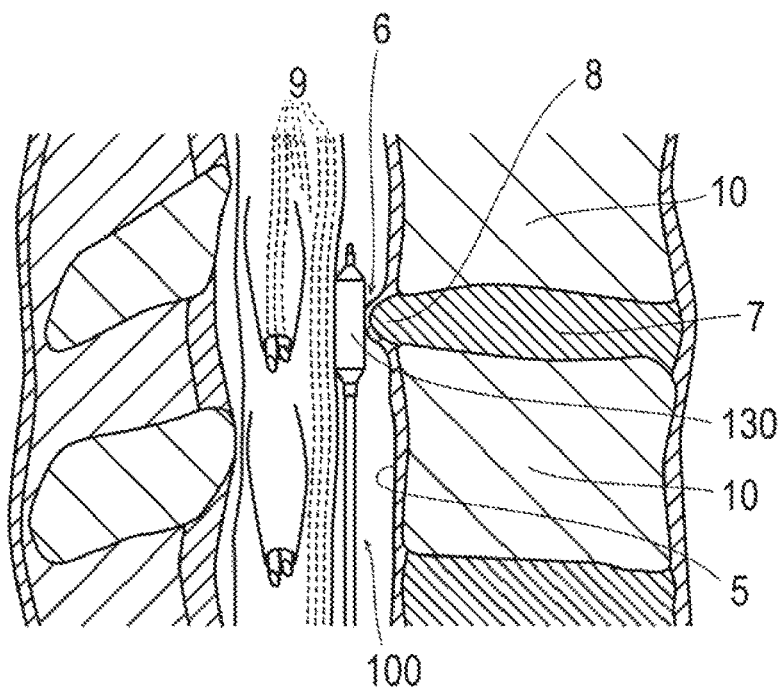
FIG. 5 is a view illustrating the insertion of the spinal treatment catheter into the treatment site.

As shown in FIG. 5, the operator moves the balloon catheter 100 forward until the balloon 130 is inserted into the treatment site 6, and implements the next treatment step S2.

Figure 6:
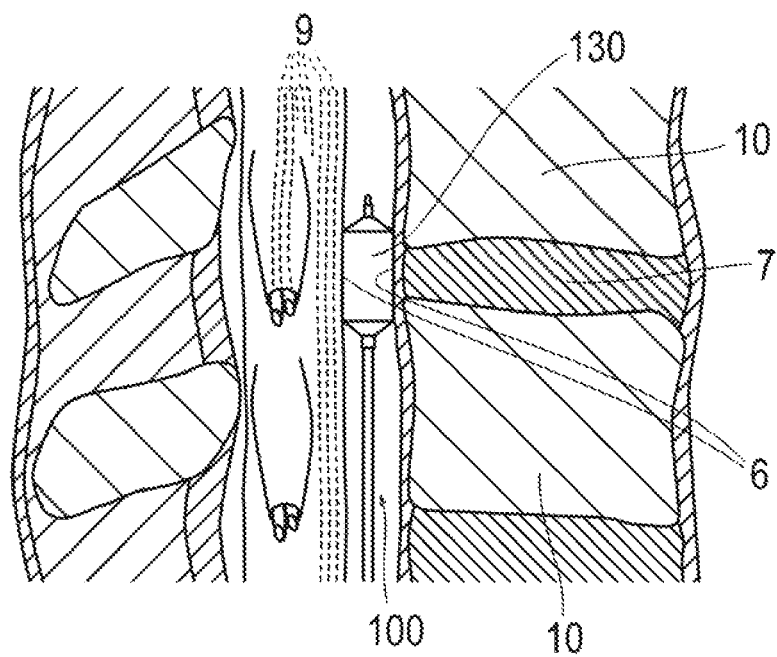
FIG. 6 is a view illustrating the dilation of a balloon at the treatment site.

As shown in FIG. 6, in the treatment step S2, the operator dilates the balloon 130 at the treatment site 6. By dilating the balloon 130, the intervertebral disk 7 which has protruded is pushed back between the vertebral bodies 10; thus, the compression on the cauda equina 9 by the hernia of intervertebral disk is mitigated.

Furthermore, as a result of the dilation of the balloon 130 and strongly pressing of the balloon 130 against the treatment site 6, the anti-inflammatory agent which has been disposed on the balloon 130 is attached and applied to the treatment site 6. The anti-inflammatory agent moves from the outer peripheral surface of the balloon 130 to an area of the hernia of the intervertebral disk 7 and to a compressed area of the cauda equina 9. The anti-inflammatory agent acts to suppress the inflammation of the treatment site 6.

A dilation pressure of the balloon 130 is not limited; however, a dilation pressure for pushing back the lesion area 8 and for the attachment of the medicine can be, for example, 1 to 50 atm.

Moreover, an axial length of the balloon 130 and an outer diameter thereof in a dilated state are not limited; however, to ensure that the balloon 130 comes in contact with and presses the treatment site 6, the axial length of the balloon 130 can be, for example, 0.5 to 10 cm and the outer diameter of the balloon 130 in the dilated state can be, for example, 1 to 10 mm. After dilating the balloon 130, the operator implements the next post-treatment step S3.

In the post-treatment step S3, the operator deflates the balloon 130 again, and removes the balloon catheter 100 from within the body to outside of the body in the deflated state. The operator stops or treats the small poriform wound that has been formed by, for example, the puncture instrument for introducing the balloon catheter 100 into the body.

Advantages and effects of the embodiments will next be described.

The compression on the cauda equina 9 is mitigated by the dilation of the balloon 130, and the inflammation of the treatment site 6 is suppressed by the anti-inflammatory agent disposed on the balloon 130. Owing to this, it is possible to remedy a disease without the surgical treatment of the treatment site 6, for example, the removal of the protruding lesion area 8 or the removal of the bone to prevent a force that possibly causes such protrusion from acting. Therefore, it is possible to treat the spine 1 in a less invasive manner and at a lower cost.

The hernia of intervertebral disk is treated, in particular; thus, it is possible to treat the hernia of intervertebral disk in a less invasive manner and at a lower cost.

Further, the balloon 130 can be inserted into the sacral canal 2 in the deflated state and the balloon catheter 100 is introduced into the target site through the sacral canal 2.

In this way, the sacral canal 2 is used for the introduction of the balloon catheter 100 into the target site; thus, it is unnecessary to form an introduction route into the target site by surgical treatment, for example, ostectomy. Therefore, it is possible to introduce the balloon catheter 100 into the target site in a less invasive manner.

Furthermore, the epidural space 5 and/or the sacral canal 2 is used to insert the balloon catheter 100; thus, it is possible to introduce the balloon catheter 100 into the target site in a minimally invasive manner.

The present invention is not limited to the abovementioned embodiments and various modifications can be made within the scope of the claims.

For example, the route of the introduction of the catheter into the treatment site is not limited to the sacral canal and the epidural space as in the abovementioned embodiment(s), and the catheter may be introduced into the target treatment site via another route.

Moreover, the disease to which the present invention is applied is not limited to the hernia of intervertebral disk. The present invention may be applied to a disease caused by the compression on nerves other than the cauda equina constituting a spinal cord, and the lesion area compressing the nerves is not limited to the intervertebral disk which has had a hernia but may be another site, for example, an incrassate ligament of the spine.

DESCRIPTION OF REFERENCE NUMERALS AND SIGNS

1 spine,
2 sacral canal,
3 sacral hiatus,
4 lumbar vertebrae,
5 epidural space,
6 treatment site,
7 intervertebral disk,
8 lesion area,
9 cauda equina (nerves extending from the spine while being bifurcated),
10 vertebral body,
100 balloon catheter (spinal treatment catheter),
110 main body portion,
111, 112 lumen,
113 marker,
120 hub portion,
130 balloon,
140 guide wire,
S1 catheter introduction step,
S2 treatment step,
S3 post-treatment step.

What is claimed is:

1. A spinal treatment method comprising:
    inserting a balloon catheter along an axis of a spine into a treatment site between nerves extending from the spine, while the nerves are being bifurcated, and a lesion area that compresses the nerves at the treatment site;
    positioning a balloon, on which an anti-inflammatory agent is disposed, of the balloon catheter at the treatment site by following the axis of the spine, wherein an axial length of the balloon is disposed in a space between the lesion area and the nerves being compressed;
    dilating the balloon in the space between the lesion area and the nerves being compressed, the balloon contacting the lesion area and the nerves being compressed along the axial length of the balloon; and
    applying, at least via the balloon contacting the lesion area and the nerves being compressed, the anti-inflammatory agent to the treatment site.

2. The spinal treatment method according to claim 1, wherein the lesion area is a herniated intervertebral disk.

3. The spinal treatment method according to claim 1, wherein inserting the balloon catheter along the axis of the spine comprises inserting the balloon catheter through a sacral canal of the spine.

4. The spinal treatment method according to claim 3, wherein inserting the balloon catheter along the axis of the spine comprises inserting the balloon catheter through an epidural space of the spine.

5. The spinal treatment method according to claim 4, wherein the lesion area is a herniated intervertebral disk.

6. The spinal treatment method according to claim 1, wherein inserting the balloon catheter along the axis of the spine comprises inserting the balloon catheter through an epidural space of the spine.

7. The spinal treatment method according to claim 6, wherein the lesion area is a herniated intervertebral disk.

8. A spinal treatment method, comprising:
    inserting a balloon catheter having a balloon disposed at a distal end thereof into a sacral hiatus of a spine;
    moving the balloon along a sacral canal of the spine and following an axis of the spine toward a treatment site, wherein a portion of the spine at the treatment site contacts and compresses nerves in the spine at a compression contact area;
    positioning an axial length of the balloon in the compression contact area;
    inflating the balloon while the balloon is positioned in the compression contact area, wherein the balloon contacts the portion of the spine and the compressed nerves in the compression contact area; and
    applying, via an anti-inflammatory agent disposed on an outer peripheral surface of the balloon, the anti-inflammatory agent to the compression contact area.

9. The spinal treatment method according to claim 8, wherein positioning the axial length of the balloon in the compression contact area comprises:
    imaging the balloon catheter using X-ray imagery; and
    locating the balloon along the spine using an X-ray contrast marker formed in a main body of the balloon catheter at the distal end thereof.

10. The spinal treatment method according to claim 8, wherein the axial length of the balloon is 0.5 mm to 10 cm.

11. The spinal treatment method according to claim 8, wherein an outer diameter of the balloon when inflated is 1 mm to 10 mm.

12. The spinal treatment method according to claim 8, wherein the portion of the spine is a herniated intervertebral disk.

13. The spinal treatment method according to claim 12, wherein inflating the balloon pushes the herniated intervertebral disk between two vertebral bodies into a compression-mitigated position.

14. The spinal treatment method according to claim 13, wherein after applying the anti-inflammatory agent to the compression contact area, the spinal treatment method further comprises:

deflating the balloon; and removing the balloon catheter from the sacral canal via the sacral hiatus.

15. A spinal treatment method, comprising:

inserting a balloon catheter having a balloon disposed at a distal end thereof into a canal of a spine, wherein the canal runs along an axis of the spine, and wherein an anti-inflammatory agent is disposed on the balloon;

moving the balloon along the canal following the axis of the spine toward a treatment site, wherein a lesion area at the treatment site contacts and compresses nerves in the spine at a compression contact area;

positioning an axial length of the balloon in the compression contact area;

inflating the balloon while the balloon is positioned in the compression contact area, wherein the balloon contacts the lesion area and the compressed nerves in the compression contact area; and applying the anti-inflammatory agent to the compression contact area while the balloon contacts the lesion area and the compressed nerves in the compression contact area.

16. The spinal treatment method according to claim 15, wherein the lesion area is a herniated intervertebral disk.

17. The spinal treatment method according to claim 16, wherein inflating the balloon pushes the herniated intervertebral disk between two vertebral bodies into a compression-mitigated position.

18. The spinal treatment method according to claim 15, wherein the canal of the spine is an epidural space.

19. The spinal treatment method according to claim 15, wherein the canal of the spine is a sacral canal, and wherein the balloon catheter is inserted into the sacral canal via a sacral hiatus.

20. The spinal treatment method according to claim 19, wherein moving the balloon along the canal following the axis of the spine toward the treatment site includes moving the balloon catheter from the sacral canal to an epidural space in the spine.

* * * * *